ers, an alkaline reagent, and a phase
United States Patent

Khouri et al.

Patent Number: 5,231,197
Date of Patent: Jul. 27, 1993

[54] METHOD FOR PRODUCING ETHYLENICALLY UNSATURATED GRAFTABLE ORTHOESTERS

[75] Inventors: Farid F. Khouri, Clifton Park, N.Y.; Robert J. Halley, Atlanta, Ga.

[73] Assignee: General Electric Company, Schenectady, N.Y.

[21] Appl. No.: 896,087

[22] Filed: Jun. 1, 1992

[51] Int. Cl.$^5$ .................. C07D 317/34; C07D 317/72; C07D 319/06
[52] U.S. Cl. ..................... 549/372; 549/375; 549/449; 549/454
[58] Field of Search ................. 549/372, 375, 449, 454

[56] References Cited

U.S. PATENT DOCUMENTS

| | | | |
|---|---|---|---|
| 3,978,088 | 8/1976 | Renner et al. | 549/372 |
| 4,048,143 | 9/1977 | Hay et al. | 260/47 |
| 4,757,132 | 7/1988 | Brunelle et al. | 528/357 |
| 4,829,144 | 5/1989 | Brunelle et al. | 528/176 |
| 4,994,525 | 2/1991 | Brown et al. | 525/66 |
| 5,098,932 | 3/1992 | Hamon | 549/449 |

Primary Examiner—C. Warren Ivy
Assistant Examiner—Ba K. Trinh
Attorney, Agent, or Firm—William H. Pittman

[57] ABSTRACT

Ethylenically unsaturated graftable monomers are prepared by reacting hydroxy substituted orthoesters with electrophilic reagents, an alkaline reagent, and a phase transfer catalyst. Preferably the hydroxy orthoester is 4-hydroxymethyl-2-methoxy-2-methyl-1,3-dioxolane, and the preferred reagent is acryloyl chloride with sodium hydroxide as the base and methyltrialkylammonium (C$_{8-10}$) chloride as the phase transfer catalyst.

12 Claims, No Drawings

METHOD FOR PRODUCING ETHYLENICALLY UNSATURATED GRAFTABLE ORTHOESTERS

This invention relates to new ethylenically unsaturated monomers, and more particularly to ethylenically unsaturated monomers containing cyclic orthoester functionality.

BACKGROUND OF THE INVENTION

In recent years, it has been desirable to produce polymers bearing orthoester functional groups. Ethylenically unsaturated cyclic orthoesters have been produced according to a method set forth in U.S. patent application Ser. No. 07/645,179, filed Jan. 24, 1991 now U.S. Pat. No. 5,171,866, however, the commercial production of these monomers presents some difficulties. For example, the reaction of hydroxy orthoester with acryloyl chloride in methylene chloride as solvent and triethylamine as an acid scavenger results in the formation of triethylammonium hydrochloride, a by-product that is difficult to remove. These ammonium salts can lead to homopolymerization of the starting hydroxy orthoester. These side reactions result in lower yields and acylated oligomers. The formation of the vinyl benzyl ethers in U.S. patent application Ser. No. 07/645,179 now U.S. Pat. No. 5,171,866 requires the use of solid sodium hydroxide. Difficulties in handling the solid sodium hydroxide and similar reagents are overcome with the method of the current invention.

The monomers obtained by the method of the current invention overcome the above-mentioned difficulties. Higher yields and improved purity of the monomers formed are a result of using a phase transfer catalysis method described in the present invention.

BRIEF DESCRIPTION OF THE INVENTION

The present invention provides an improved method of making a series of ethylenically unsaturated monomers which may be employed in the preparation of a wide variety of functionalized polymers. These graftable monomers contain highly reactive orthoester groups as substituents, which remain in the polymers prepared therefrom. Once grafted, the orthoester groups can undergo reaction with numerous other polymers, forming copolymer-containing compositions with excellent properties.

Accordingly, the invention is a method for preparing a graftable ethylenically unsaturated orthoester comprising reacting a hydroxy-substituted orthoester of the formula

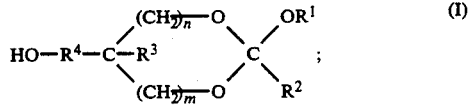

wherein:
each of $R^1$ and $R^2$ is $C_{1-10}$ primary or secondary alkyl or aralkyl, or a $C_{6-10}$ aromatic radical or $R^1$ and $R^2$ together with atoms connecting $R^1$ and $R^2$ together form a ring;

$R^3$ is hydrogen or $C_{1-4}$ primary or secondary alkyl radical as defined above for $R^2$, or a $C_{6-10}$ aromatic radical;

$R^4$ is an unsubstituted or substituted $C_{1-6}$ alkylene or $C_{6-10}$ arylene radical; m is 0 or 1; n is from 1 to $2-m$;

with an electrophilic reagent of the formula

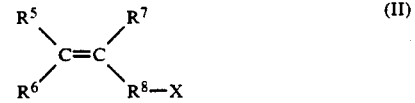

wherein $R^5$, $R^6$ and $R^7$ are the same or different and are hydrogen; or a $C_{1-8}$ alkyl radical or substituted derivatives thereof; or an aryl radical or substituted derivative thereof; $R^8$ is a $C_{1-6}$ alkylene group, a carbonyl group, or an aralkylene group, or mixtures thereof; and X is a leaving group; in the presence of a phase transfer catalyst and an alkaline reagent.

DETAILED DESCRIPTION OF THE INVENTION

Suitable hydroxy-substituted orthoesters for use in the current invention have formula (I) as described above.

The $R^1$ and $R^2$ radical may be a $C_{1-4}$ primary or secondary alkyl radical such as methyl, ethyl, n-propyl, isopropyl, n-butyl, isobutyl, or secondary butyl. Primary radicals and especially the methyl radical are generally preferred. The $R^3$ may be a $C_{1-4}$ primary or secondary alkyl radical as defined above for $R^2$, or a $C_{6-10}$ aromatic (preferably aromatic hydrocarbon) radical. Finally, it is possible for $R^1$ and $R^2$ together to form a 5-, 6- or 7-membered ring with the atoms connecting them. Thus, certain spiroorthoester derivatives are also encompassed by this formula.

The values of m and n depend on whether the cyclic orthoester moiety is a 5-membered or 6-membered ring. In general, 5-membered rings are preferred; that is, m is 0 and n is 1. However, compositions in which a 6-membered ring is present, which requires either that m and n both be one or that m be 0 and n be 2 may also be used.

The hydroxy orthoester can be prepared according to conventional methods known to the art. One method of making the hydroxy orthoester is disclosed in Ser. No. 07/623,838, filed Dec. 7, 1990 now abandoned, in which the hydroxy orthoester is made by contacting under reactive conditions, an aliphatic triol with at least an equimolar amount of an orthoester in the presence of an acidic catalyst. The preferred hydroxy orthoester is 4-hydroxymethyl-2-methoxy-2-methyl-1,3-dioxolane.

The hydroxy-substituted orthoesters are reacted with a reagent of formula (II) described above. The preferred reagent is acryloyl chloride.

The substituent X may be any leaving group which is known to undergo nucleophilic substitution. Those skilled in the art will understand that a wide variety of groups fit this description, and the invention is not limited in that respect. Examples of leaving groups include halogens; sulfonate esters, such as p-toluene, p-nitrobenzene, p-bromobenzene, methane sulfonate, and the like; and fluorinated sulfonate esters such as trifluoromethane sulfonate and the like. The preferred X group is a halogen atom, and more preferably chlorine.

The reaction between the hydroxy orthoester and the electrophilic reagent is conducted under conventional conditions, typically in the presence of an alkaline reagent such as sodium hydroxide. The hydroxy orthoester and reagent can be employed in roughly equimolar amounts, or a 10–20 percent excess of one or the other may be employed. Optionally, a solvent may be used.

When the electrophilic reagent is an acid chloride, the reaction typically occurs in the presence of a relatively non-polar organic solvent. Examples of such solvents include methylene chloride, and toluene.

Generally the reaction temperature for forming the graftable orthoester monomers depends on whether the reaction is an etherification reaction or an acylation reaction. The reaction typically occurs at a temperature range of from about 25° C. to about 100° C., and preferably at about 50° C. If the reaction involves an acylation, the reaction typically occurs in a range of about −10° C. to about 50° C. and preferably occurs at 0° C. However, one skilled in the art would contemplate the use of other solvents that might require a temperature adjustment.

An essential feature of the invention is the use of a phase transfer catalyst during the synthesis of the ethylenically unsaturated monomers. Any phase transfer catalyst which is stable and effective under the prevailing reaction conditions may be used. Examples of phase transfer catalysts include ammonium salts, phosphonium salts, hexaalkyl guanidinium halides and crown ethers. Preferred are the quaternary ammonium salts. Representative quaternary ammonium salts are tetraalkylammonium halides containing a total of about 15–30 carbon atoms, examples of which are tetra-n-butylammonium bromide and methyltrioctylammonium chloride. A preferred phase transfer catalyst is ADOGEN 464 ® available from Ashland Chemical Company, which is a methyltrialkylammonium chloride wherein the alkyl groups have from about 8 to 10 carbon atoms.

The preparation of the orthoesters of this invention is illustrated by the following examples. Molecular structures of all products in Examples 1–5 were confirmed by proton and carbon-13 nuclear magnetic resonance spectroscopy.

EXAMPLE 1

A 3-necked 2 liter round-bottomed flask was equipped with a mechanical stirrer, condenser, thermometer, and addition funnel. The flask was charged with 2.5 g methyltrialkylammonium chloride ($C_8$–$C_{10}$), 500 mL toluene, 160 mL distilled water, and 165 g of 50 percent aqueous sodium hydroxide. The flask was immersed in an ice-water bath and cooled to approximately 10° C. while stirring rapidly. 150 g (1.01 mol) 4-hydroxymethyl-2-methoxy-2-methyl-1,3-dioxolane was charged into the flask. 109 g acryloyl chloride (1.20 mol) was dripped into the flask via the addition funnel over a 60 minute period maintaining the reaction temperature at approximately 10° C. or lower. After the addition of the acid chloride was complete, the reaction was stirred for 10 additional minutes. The layers were separated, 5 mL of triethylamine was added to the toluene layer. The toluene layer was washed twice with 500 mL distilled water, dried over anhydrous magnesium sulfate, vacuum stripped and yielded 205 g product. The desired 4-hydroxymethyl-2-methoxy-2-methyl-1,3-dioxolane acrylate ester distilled at 75°–85° C./0.5–1.0 torr.

EXAMPLE 2

A 3-necked, 250 mL round-bottomed flask equipped with a mechanical stirrer, condenser, thermometer, and addition funnel was charged with 0.25 g methyltrialkylammonium chloride ($C_{8-10}$), 30 mL toluene, 16 mL water, and 16.5 g of 50 percent aqueous sodium hydroxide. The flask was placed into an ice bath and cooled to approximately 10° C. 15 g 4-hydroxymethyl-2-methoxy-2-methyl-1,3-dioxolane (1.101 mol) was added. 20 g cinnamoyl chloride (0.120 mol) dissolved in toluene was dripped via the addition funnel over a 25 minute period maintaining the reaction temperature at or below 10° C. The reaction temperature was then raised to room temperature, and the layers were separated. 1 mL triethylamine was added to the toluene layer. This layer was washed two times with 50 mL distilled water, dried over anhydrous magnesium sulfate, vacuum stripped and yielded 16.37 g of product. The desired 4-hydroxymethyl-2-methoxy-2-methyl-1,3-dioxolane cinnamoate ester distilled at 165°–170° C./0.5–1.0 torr.

EXAMPLE 3

A 3-necked, 250 mL round-bottomed flask equipped with a reflux condenser and two pressure equalizing addition funnels was charged with 60 mL of a 30 percent by weight aqueous sodium hydroxide solution and 1.275 gram (4.1 mmol) of benzyltributylammonium chloride. 4-hydroxymethyl-2-methoxy-2-methyl-1,3-dioxolane (29.14 g, 196.7 mmol) and 25 g vinylbenzyl chloride (164 mmol) were simultaneously charged under a nitrogen atmosphere from the addition funnels into the flask over a 5 minute period. The reaction flask was immersed in an oil bath at 50° C. and the contents were stirred for 6 hours, then stirred at room temperature overnight. The organic phase was separated, diluted with methylene chloride (200 mL) and triethylamine (5 mL), washed with water, dried over anhydrous magnesium sulfate, and vacuum stripped. 42 g of 4-hydroxymethyl-2-methoxy-2-methyl-1,3-dioxolane vinylbenzyl ether were produced.

EXAMPLE 4

The procedure of Example 3 was repeated, employing 17.78 g of hydroxy orthoester (120 mmol), 15.26 g of cinnamyl chloride (100 mmol) with 36 mL of 30 percent aqueous sodium hydroxide and 0.7 g benzyltriethylammonium chloride. The reaction was run at a temperature of 50° C. for 1.5 hours, and was worked up as in Example 3 to give 25 g of product. This product was then distilled under vacuum to give 4-hydroxymethyl-2-methoxy-2-methyl-1,3-dioxolane cinnamyl ether at 135°–142° C./0.2 torr.

EXAMPLE 5

The procedure of Example 4 was repeated, employing 22.22 g of hydroxy orthoester (150 mmol), 13.775 g allyl chloride (180 mmol) in 45 mL aqueous sodium hydroxide and 0.85 g benzyltriethylammonium chloride. The reaction temperature was maintained at 50° C. for 11 hours. The product was isolated as in the preceding examples and distilled under vacuum to yield 17.8 grams of 4-hydroxymethyl-2-methoxy-2-methyl-1,3-dioxolane allyl ether at 55° C./0.3 torr.

The graftable orthoesters of the present invention may be reacted with polyphenylene ether comonomers. This results in the formation of the novel polyphenylene ether-graft-orthoester polymers as described in copending, commonly owned application Ser. No. 07/863,625, filed Apr. 3, 1992. Further, the polyphenylene ether graft-orthoester (PPE-G-OE) may be further reacted with nucleophilic polymers, particularly polyesters, polyamides, or functionalized polyolefins. The blends of nucleophilic polymers is described in copending, commonly owned application Ser. No. 07/863,624, filed Apr. 3, 1992.

What is claimed is:

1. A method for preparing graftable ethylenically unsaturated orthoesters comprising reacting a hydroxy-substituted orthoester of the formula

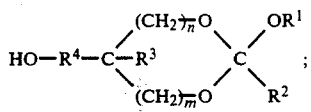

wherein:
each of $R^1$ and $R^2$ is $C_{1-10}$ primary or secondary alkyl or aralkyl, or a $C_{6-10}$ aromatic radical or $R^1$ and $R^2$ together with atoms connecting $R^1$ and $R^2$ together form a ring;
$R^3$ is hydrogen or $C_{1-4}$ primary or secondary alkyl radical as defined above for $R^2$, or a $C_{6-10}$ aromatic radical;
$R^4$ is an unsubstituted or substituted $C_{1-6}$ alkylene or $C_{6-10}$ arylene radical; m is 0 or 1; n is from 1 to $2-m$;
with an electrophilic reagent of the formula

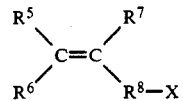

wherein $R^5$, $R^6$ and $R^7$ are the same or different and are hydrogen; or a $C_{1-8}$ alkyl radical or substituted derivatives thereof; or an aryl radical or substituted derivative thereof; $R^8$ is a $C_{1-6}$ alkylene group, a carbonyl group, or an aralkylene group, or mixtures thereof; and X is a leaving group; in a nonpolar organic solvent and in the presence of a phase transfer catalyst and an alkaline reagent; the molar ratio of said orthoester to said electrophilic reagent being from 1.2:1 to 1:1.2.

2. The method of claim 1 wherein $R^1$ is methyl.

3. The method of claim 2 wherein $R^2$ is methyl.

4. The method of claim 2 wherein m is 0 and n is 1.

5. The method of claim 3 wherein $R^3$ is hydrogen and $R^4$ is methylene.

6. The method of claim 1 wherein said hydroxy orthoester is 4-hydroxymethyl-2-methoxy-2-methyl-1,3-dioxolane.

7. The method of claim 1 wherein said reagent is acryloyl chloride.

8. The method of claim 1 wherein the phase transfer catalyst is a quaternary ammonium salt.

9. The method of claim 8 wherein said organic solvent is methylene chloride or toluene.

10. The method of claim 1 wherein said reaction occurs at a temperature of from about 25°–100° C.

11. The method of claim 1 wherein said reaction occurs at a temperature of from about −10° to about 50° C.

12. The method of claim 1 wherein said phase transfer catalyst is methyltrialkylammonium chloride wherein the alkyl groups have from about 8 to about 10 carbon atoms.

* * * * *